(12) United States Patent
Won et al.

(10) Patent No.: US 11,497,764 B2
(45) Date of Patent: *Nov. 15, 2022

(54) POLYMER LUNG SURFACTANTS

(71) Applicant: Purdue Research Foundation, West Lafayette, IN (US)

(72) Inventors: You-Yeon Won, West Lafayette, IN (US); Hyun Chang Kim, Wilmington, DE (US)

(73) Assignee: Purdue Research Foundation, West Lafayette, IN (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/107,295

(22) Filed: Nov. 30, 2020

(65) Prior Publication Data

US 2021/0187010 A1     Jun. 24, 2021

Related U.S. Application Data

(60) Division of application No. 16/660,179, filed on Oct. 22, 2019, now abandoned, which is a division of
(Continued)

(51) Int. Cl.
*A61K 9/08*         (2006.01)
*A61P 11/00*        (2006.01)
(Continued)

(52) U.S. Cl.
CPC .......... *A61K 31/765* (2013.01); *A61K 9/0019* (2013.01); *A61K 9/0082* (2013.01);
(Continued)

(58) Field of Classification Search
CPC .. A61K 2300/00; A61K 31/74; A61K 31/765; A61K 31/77; A61K 31/78;
(Continued)

(56) References Cited

U.S. PATENT DOCUMENTS

| | | |
|---|---|---|
| 5,770,627 A | 6/1998 | Inoue |
| 6,180,142 B1 | 1/2001 | Taeusch |

(Continued)

FOREIGN PATENT DOCUMENTS

| | | |
|---|---|---|
| CA | 3032457 A1 | 2/2018 |
| EP | 3496732 A1 | 6/2019 |

(Continued)

OTHER PUBLICATIONS

U.S. Appl. No. 15/881,723, U.S. Pat. No. 10,485,820, filed Jan. 26, 2018, Polymer Lung Surfactants.

(Continued)

*Primary Examiner* — Ernst V Arnold
(74) *Attorney, Agent, or Firm* — Schwegman Lundberg & Woessner, P.A.

(57) ABSTRACT

Disclosed herein are fully synthetic polymer-based lung surfactant materials, for the first time, as next generation SRT. In vitro studies on these polymer lung surfactants show that the candidate materials effectively mimic the surface tension controlling properties of currently marketed natural lung surfactants. Further, the polymer lung surfactants have strong protein resistance, which makes this class of materials promising also for potential use in Acute Respiratory Distress Syndrome (ARDS) treatment.

8 Claims, 12 Drawing Sheets

Related U.S. Application Data application No. 15/881,723, filed on Jan. 26, 2018, now Pat. No. 10,485,820, which is a continuation-in-part of application No. PCT/US2017/046426, filed on Aug. 11, 2017.

(60) Provisional application No. 62/374,325, filed on Aug. 12, 2016.

(51) Int. Cl.

| | | |
|---|---|---|
| *A61K 31/765* | (2006.01) | |
| *A61K 9/00* | (2006.01) | |
| *A61K 9/107* | (2006.01) | |
| *A61K 47/34* | (2017.01) | |

(52) U.S. Cl.
CPC ............. *A61K 9/08* (2013.01); *A61K 9/107* (2013.01); *A61K 9/1075* (2013.01); *A61K 47/34* (2013.01); *A61P 11/00* (2018.01)

(58) Field of Classification Search
CPC ...... A61K 31/787; A61K 45/06; A61K 47/34; A61K 9/0019; A61K 9/0082; A61K 9/08; A61K 9/107; A61K 9/1075; A61P 11/00
See application file for complete search history.

(56) References Cited

U.S. PATENT DOCUMENTS

| | | | |
|---|---|---|---|
| 6,939,564 | B2 | 9/2005 | Ranger |
| 10,485,820 | B2 * | 11/2019 | Won .......................... A61K 9/08 |
| 2013/0004453 | A1 | 1/2013 | Gellman |
| 2013/0228181 | A1 | 9/2013 | Ahmad et al. |
| 2018/0153926 | A1 | 6/2018 | Won et al. |
| 2020/0046756 | A1 | 2/2020 | Won et al. |

FOREIGN PATENT DOCUMENTS

| | | | |
|---|---|---|---|
| WO | 97/10849 | A1 | 3/1997 |
| WO | WO-97/10849 | A1 | 3/1997 |
| WO | 2010/046681 | A1 | 4/2010 |
| WO | WO-2010/046681 | A1 | 4/2010 |
| WO | 2013/106100 | A1 | 7/2013 |
| WO | WO-2013/106100 | A1 | 7/2013 |
| WO | WO-2018/031850 | A1 | 2/2018 |

OTHER PUBLICATIONS

U.S. Appl. No. 16/660,179, filed Oct. 22, 2019, Polymer Lung Surfactants.
Griese, EurResp J 13: 1455-1476 (1999).
Hertzog et al., The Journal of Extra-Corporeal Technology 28(2): 94-98 (1996).
Skillrud et al., Mayo Clin Proc 60:266-269 (1985).
Han et al., Arch Pharm Res 30(10): 1344-1349 (2007).
Lekkala et al., Infection and Immunity 74(8): 4549-4556 (2006).
Dhand, The Role Aerosolized Antimicrobials in the Treatment of Ventilator-Associated Respiratory Care 52(7): 866-884 (2007).
Moen et al., Drugs 69(3): 361-392 (2009).
Park et al., Langmuir 28:11555-11566 (2012).
Logie et al., Chemistry of Materials 26(9): 2847-2855 (2014).
Moretton et al., Journal of the Royal Society Interface 9(68): 487-502 (2012).
Hussain et al., Langmuir 24:13279-13286 (2008).
Kim et al., Langmuir 31(51): 13821-13833 (2015).
Cox et al., Langmuir 15(22): 7714-7718 (1999).
Malzert et al., Langmuir 17(25): 7837-7841 (2001).
Ranger et al., J of Polymer Sci, Part A: Polymer Chemistry 39(22): 3861-3874 (2001).
Kim et al., ACS Applied Bio Materials 1(3): 581-592 (2018).
Purdue Research Foundation, WO 2018/031850 (PCT/US2017/046426) international search report and written opinion (int'l pat app pub date Feb. 15, 2018).
Purdue Research Foundation, EP 3496732 (EP App No. 17840318) extended European search report and opinion (EP pat app pub date Jun. 19, 2019).
Moya, J of Perinatology 29: S23-S28 (2009).
"International Application Serial No. PCT/US2017/046426, International Preliminary Report on Patentability dated Feb. 21, 2019", 9 pgs.
"International Application Serial No. PCT/US2017/046426, International Search Report dated Oct. 23, 2017", 2 pgs.
"International Application Serial No. PCT/US2017/046426, Written Opinion dated Oct. 23, 2017", 7 pgs.
"Japanese Application Serial No. 2019-507101, Written Opinion and Amendment filed Jul. 19, 2021 in response to Notification of Reasons for Refusal dated Jan. 19, 2021", (w/ English Translation), 41 pgs.
"U.S. Appl. No. 15/881,723, Advisory Action dated Sep. 23, 2019", 7 pgs.
"U.S. Appl. No. 15/881,723, Final Office Action dated May 15, 2019", 21 pgs.
"U.S. Appl. No. 15/881,723, Non-Final Office Action dated Feb. 6, 2019", 16 pgs.
"U.S. Appl. No. 15/881,723, Notice of Allowance dated Oct. 10, 2019", 9 pgs.
"U.S. Appl. No. 15/881,723, Response filed Jan. 10, 2019 to Restriction Requirement dated Nov. 16, 2018", 7 pgs.
"U.S. Appl. No. 15/881,723, Response filed Apr. 17, 2019 to Non-Finai Office Action dated Feb. 6, 2019", 10 pgs.
"U.S. Appl. No. 15/881,723, Response filed Sep. 3, 2019 to Final Office Action dated May 15, 2019", 11 pgs.
"U.S. Appl. No. 15/881,723, Restriction Requirement dated Nov. 16, 2018", 12 pgs.
"U.S. Appl. No. 16/660,179, Examiner Interview Summary dated Sep. 16, 2020", 4 pgs.
"U.S. Appl. No. 16/660,179, Non-Final Office Action dated Jul. 29, 2020", 19 pgs.
"U.S. Appl. No. 16/660,179, Response filed Jul. 13, 2020 to Restriction Requirement dated Jul. 6, 2020", 2 pgs.
"U.S. Appl. No. 16/660,179, Restriction Requirement dated Jul. 6, 2020", 11 pgs.
"European Application Serial No. 17840318.4, Extended European Search Report dated Apr. 7, 2020", 11 pgs.
"European Application Serial No. 17840318.4, Office Action dated Apr. 24, 2020", 1 pg.
"European Application Serial No. 17840318.4, Response filed Oct. 19, 2020 to Office Action dated Apr. 24, 2020", 13 pgs.
"Japanese Application Serial No. 2019-507101, Notification of Reasons for Refusal dated Jan. 19, 2021", (w/ English Translation), 11 pgs.
"Japanese Application Serial No. 2019-507101, Examiners Decision of Final Refusal dated Nov. 30, 2021", (w/ English Translation), 10 pgs.
Murayama, Keiko, et al., "Assessment of dysphagia in the patient with cerebral palsy—A Chart to Estimate the Possibility of Aspiration in patients with severe motor and intellectual disabilities", (w/ English Abstract), Journal of Eating and Swallowing Association, vol. 8, No. 2, (2004), 143-155.
Taniguchi, Akihiro, et al.,"Spinal anesthesia for infants and children", (w/ English Abstract), Journal of Japanese Clinical Anaesthellants, vol. 8, No. 4, (1988), 440-445.

* cited by examiner

| Polymer | $M_{n,PEG}$ (g/mol) | $M_{n,PLGA/PS}$ (g/mol) | PDI |
|---|---|---|---|
| PLGA(4030)-PEG(5000) | 5,000 | 4,030† | 1.41 |
| PS(1560)-PEG(5000) | 5,000 | 1,560 | 1.10 |
| PS(2993)-PEG(5000) | 5,000 | 2,993 | 1.13 |
| PS(4418)-PEG(5000) | 5,000 | 4,418 | 1.34 |
| PS(5610)-PEG(5000) | 5,000 | 5,610 | 1.16 |
| PS(13832)-PEG(5000) | 5,000 | 13,832 | 1.38 |

POLYMER LUNG SURFACTANTS

CROSS-REFERENCE TO RELATED APPLICATIONS

This application is a divisional of U.S. patent application Ser. No. 16/660,179, which was filed on Oct. 22, 2019, as a divisional application of U.S. patent application Ser. No. 15/588,723, which was filed on Jan. 26, 2018, as a continuation-in-part of PCT application PCT/US2017/046426, which was filed on Aug. 11, 2017, and which claims the benefit of U.S. provisional patent application No. 62/374,325, filed on Aug. 12, 2016, all contents of which are hereby incorporated by reference in their entireties.

STATEMENT ON GOVERNMENT FUNDING

This invention was made with government support under CBET-1264336 awarded by the National Science Foundation. The government has certain rights in the invention.

TECHNICAL FIELD

The present disclosure generally relates to polymer lung surfactants and in particular to polymer lung surfactant materials that satisfy all surfactant performance requirements and have better handling characteristics than current respiratory distress syndrome therapeutics.

BACKGROUND

This section introduces aspects that may help facilitate a better understanding of the disclosure. Accordingly, these statements are to be read in this light and are not to be understood as admissions about what is or is not prior art.

Infants who are born before the full 40-week gestation period are considered "preterm" (if born before week 37 of pregnancy) or "premature" (if born before 34-week gestation). One of the major health risks associated with preterm/premature births is underdeveloped lungs, which cause high infant mortality. Infants born before the 37th week of gestation are born without alveolar structures, and have low production of lung surfactants. As a result, preterm/premature infants struggle to breathe, and, without proper treatments, die within a few days. This respiratory failure is named as Respiratory Distress Syndrome (RDS), or also known as Hyaline Membrane Disease, misnamed in the past due to the misconception of the cause of this disease as being of viral origin.

In old days when RDS was misnamed as Hyaline Membrane Disease, it was the leading cause of infant death in the United States with a higher death rate than Pneumonia and Influenza. However, now-a-days with skilled physicians and three well-established treatment methods, the mortality rate from RDS decreased substantially. The three treatments are performed in stages where if the earlier treatment is successful the next treatment is not performed. The first treatment for RDS is a prevention treatment where steroid is given to the mother 24 hours prior to labor to increase the production of the infant's own lung surfactants. Clinical data on steroid treatment with betamethasone has shown effective reduction of RDS occurrence from 25.8% to 9.0%. The second treatment, Surfactant Replacement Therapy (SRT), involves intratracheal injection of animal extracted lung surfactants into the infant's lungs immediately after birth. The development of successful SRT has been the main driver in lowering the RDS-related mortality rate, and, due to its high effectiveness, is included in the Essential Drug List of the World Health Organization. The third treatment involves mechanical ventilation in which infants are put under nasal continuous/discontinuous positive airway pressure treatment to increase the oxygen levels in the lungs. Treatment using mechanical ventilation is the oldest treatment method for treating RDS. Its initial clinical testing was shown to reduce the mortality rate from 80% to 20%. However, oxygen poisoning and mechanical damage to the lungs remain an adverse effect. Out of the three treatment methods, SRT is the most reliable treatment directly resolving the underlying cause of RDS with no adverse effect reported so far. Improvement of RDS treatment is expected to be accompanied with advancements in SRT practice.

Despite the success in the domestic reduction of the RDS-related mortality for preterm and premature infants, world-wide, especially in developing countries, RDS is currently still one of the leading causes of neonatal death due to the high treatment cost and complex treatment procedures. Although highly effective, the cost of SRT is extremely high; the cost of SRT therapeutics alone exceeds the per capita GNP in some countries. The economical imbalance affecting the use of SRT is clearly shown in FIG. 1 where countries in Central Asia and Africa do not have full access to SRT. Development of lower-cost RDS therapeutics with simpler treatment procedures that do not require highly skilled physicians and advanced neonatal intensive care units (NICU) will solve this problem, and will reduce the leading cause of neonatal death world-wide. It should be noted that even in the United States, in some rural areas, preterm and premature infants are exposed to risks of RDS-related mortality due to the lack of skilled physicians and needed medical resources such as NICU facilities. In regions where SRT is not practicable, treatment mainly relies on mechanical ventilation. There is therefore an unmet need for a better SRT technology.

Lung Surfactant (LS) complication can also occur in adults and pediatrics. The most severe form of respiratory failure is termed acute respiratory distress syndrome (ARDS). ARDS is a physiological syndrome that involves multiple risk factors such as sepsis, pneumonia, aspiration-induced lung injury, lung contusion, and massive transfusion. The annual US prevalence of ARDS is 190,000, and despite modern critical care, the mortality rate is ~40%. Regardless of the origin, ARDS patients exhibit increased protein-rich exudates and inflammation in the alveoli, which result in inactivation and reduced production of lung surfactant. With the success in treatment of neonatal RDS (NRDS) infants with therapeutic LSs, a number of clinical trials investigated their efficacy in treating ARDS patients. Unfortunately, the results from large-scale clinical trials have indicated that current therapeutic LSs are not effective in treating adult ARDS. However, there were two critical issues with previous clinical trials. (1) Current therapeutic LSs are not designed to be resistant to deactivation caused by serum proteins. (2) The LS dose levels used were inappropriate. Both of these factors are related to the mechanism of LS's surface activity.

There is a need for an alternative method for ARDS treatment: the use of therapeutic surfactants that are resistant to deactivation by proteins. All currently available lipid/protein-based LSs fall short in this regard.

SUMMARY

This disclosure provides a method of treating pulmonary disorders, including infant, acute or adult respiratory distress syndromes, caused by deficiency and/or deactivation of functional lung surfactant in mammals, including humans. The method includes administering to an animal or human subject a therapeutically effective amount of polymer lung surfactant composition. The polymer lung surfactant composition comprises an effective amount of a synthetic biocompatible or biodegradable amphiphilic homopolymer or copolymer whose monomers are selected from the group consisting of: ethylene glycol (EG), ethylene oxide (EO), vinyl alcohol (VA), alkyl oxazoline (AO), D,L-lactic acid or D,L-lactide (LA), glycolic acid or glycolide (GA), ε-caprolactone (CL), styrene (PS), alkyl methacrylate (AMA), alkyl acrylate (AA), butadiene (BD), and isoprene (IP).

Another method of treating pulmonary disorders, including infant, acute or adult respiratory distress syndromes, caused by deficiency and/or deactivation of functional lung surfactant in mammals, including humans, wherein the method includes administering to an animal or human subject a synthetic block copolymer as a single therapeutic agent or in combination with other therapeutics.

Yet another method of treating pulmonary disorders, including infant, acute or adult respiratory distress syndromes, caused by deficiency and/or deactivation of functional lung surfactant in mammals, including humans, includes administering to an animal or human subject a synthetic random copolymer to the subject as a single therapeutic agent or in combination with other therapeutics.

Another method of treating pulmonary disorders, including infant, acute or adult respiratory distress syndromes, caused by deficiency and/or deactivation of functional lung surfactant in mammals, including humans, wherein the method includes administering to an animal or human subject a synthetic homopolymer to the subject as a single therapeutic agent or in combination with other therapeutics.

Yet another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(styrene-block-ethylene glycol) (PS-PEG) block copolymer.

Another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(tert-butyl methacrylate-block-ethylene glycol) (PtBMA-PEG) block copolymer.

Another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(D,L-lactic acid-block-ethylene glycol) (PLA-PEG) block copolymer.

A method of treating pulmonary disorders, including infant, acute or adult respiratory distress syndromes, caused by deficiency and/or deactivation of functional lung surfactant in mammals, including humans, wherein the method includes administering to an animal or human subject, a polymer lung surfactant composition to the lungs of the animal or human subject in the form of an aqueous solution via endotracheal instillation.

A method of treating pulmonary disorders, including infant, acute or adult respiratory distress syndromes, caused by deficiency and/or deactivation of functional lung surfactant in mammals, including humans, wherein the method includes including administering to an animal or human subject a polymer lung surfactant composition to the patient's lungs in the form of liquid drop or lyophilized powder-type aerosols through application of continuous positive airway pressure.

Exemplary polymer lung surfactant composition used in above method of treatment have a formulation comprising, at the time of administration to a patient, about 0.02-40 wt. % amphiphilic block copolymers dispersed in micelle form in aqueous saline solution, wherein the amphiphilic block copolymer compound comprises a hydrophilic block (e.g., PEG) having an average molecular weight in the range between about 50 Da and about 1000 kDa and a hydrophobic block (e.g., PS) having an average molecular weight in the range between about 50 Da and about 1000 kDa.

DESCRIPTION

Figure 1:
FIG. 1. Countries in which Surfactant Replacement Therapy (SRT) is currently being practiced are colored in green. Countries were marked as "SRT practicing" if patients have access to at least one marketed lung surfactant therapeutic. Data were collected using Medtrack on Mar. 24, 2015.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Since the initial development of animal-derived RDS therapeutics in 1980s, little further progress has been achieved in this field. Aerosol delivery and synthetic protein replacement have been the main thrust in research, but efforts have met with limited success. Testing fully synthetic polymer materials in SRT represents a radical shift in the direction of lung surfactant research. Polymer lung surfactants may open the door to new therapeutic options for the treatment of RDS that had not previously been feasible with conventional lipid-based SRT therapeutics. Polymer lung surfactants can easily be aerosolized in liquid or powder form; in the drug delivery literature, such polymers as PS, PLGA and PLGA-PEG have been frequently used as excipients for pulmonary drug delivery.[64-69] Polymer lung surfactant formulations can also be used to co-deliver additional therapeutic agents which carry a risk of causing lung surfactant deactivation when delivered alone.

What is possibly the greatest advantage is that the reversible and hysteretic surface tension lowering effects observed with the PS-PEG and poly(t-butyl methacrylate-block-ethylene glycol) (PtBMA-PEG) systems could be achieved with other, wider choices of chemistries, creating opportunities for further improvements and new applications of this technology.

Figure 2:
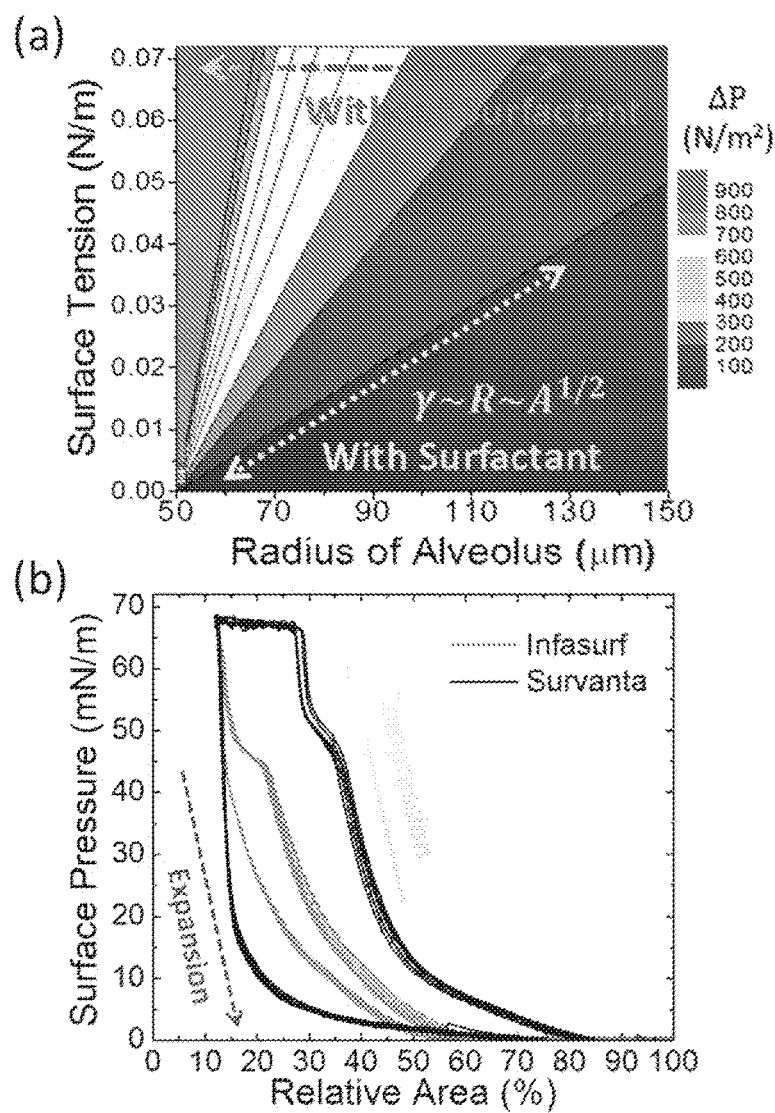
FIG. 2. (a) Contour plot of the Laplace pressure (ΔP) of a spherical alveolus calculated as a function of surface tension (γ) and radius (R). (b) Surface pressure vs. relative area isotherms of Infasurf and Survanta obtained during repeated continuous compression-expansion cycles. The data displayed represent the last 10 compression-expansion cycles of total 50 continuous cycles. The subphase solution used contained 150 mM NaCl, 2 mM $CaCl_2$, and 0.2 mM $NaHCO_3$ (pH 7.0 -7.4, 25° C.). The monolayer was compressed/expanded at a rate of 50 mm/min; one compression-expansion cycle took 7.18 minutes. At the "100% relative area", 10 mg of Infasurf/Survanta was spread on water in a Langmuir trough with 780 $cm^2$ surface area and 1.4 L subphase volume; "100% relative areas" corresponded to 0.972 $Å^2$/molecule for both Infasurf and Survanta.

Although therapeutic Lung Surfactants from animal sources and endogenous human LSs are different slightly in composition, they both overall contain about 90% phospholipids and 10% surfactant proteins. The phospholipids reside at the air-water interface, and lower the air-water interfacial tension proportionally to the radius of the alveolus (and thus to the square root of the surface area of the alveolus). The size-dependent reduction of the air-water interfacial tension consequently equalizes the Laplace pressure (ΔP) between differently sized alveoli, as shown in FIG. 2(a). The air-water interfacial mechanical properties of LSs are typically studied by measurements of surface pressure versus area isotherms during compression-expansion cycles. The surface pressure-relative area isotherms for two commercial therapeutic surfactants, Infasurf® (ONY) and Survanta® (AbbVie), are shown in FIG. 2(b). Here, the surface pressure ($\pi$) is defined as the difference between the surface tension of the clean air-water interface ($\gamma_0$) and that of the LS-laden air-water interface ($\gamma$), that is, $\pi=\gamma_0-\gamma$. For both Infasurf and Survanta, a sharp increase in surface pressure (sharp decrease in surface tension) was observed upon compression, while a sharp decrease in surface pressure (sharp increase in surface tension) was seen upon expansion.

During compression-expansion cycles, phospholipids desorb from the air-water interface at high compression, and readsorb to the air-water interface upon expansion (with the aid of surfactant proteins). It is this desorption-readsorption mechanism that makes lipid/protein-based LSs susceptible to deactivation, and complicates dose estimation for ARDS treatment. Typically the lungs of an ARDS patient are flooded with fluids rich in albumin, fibrinogen and hemoglobulin (collectively referred to as "deactivating agents"). These deactivating agents have a higher tendency to adsorb to the air-water interface than LS lipids. Thus, after a few breathing cycles, LSs at the air-water interface are replaced by these deactivating proteins. In previous ARDS clinical trials, high doses of therapeutic LSs have typically been used with the hope that the excess amount of LSs leads to a re-replacement of the deactivating agents at the air-water interface by the therapeutic surfactants. However, clinical data suggest that this is not an effective strategy.

The desorption-readsorption mechanism also poses a problem in estimating the optimal dose. If the same dosing strategy for therapeutic LSs is used in adult ARDS patients as that used in NRDS infants, the recommended dose is 100 mg of phospholipids per kg of body weight; in terms of injection volume, the number becomes 3-4 ml of LS suspension per kg of body weight. The "100 mg/kg" dose represents an amount that is about 32 times excess than that needed to fully coat the whole surface area of the lungs of an infant (3.1 mg/kg). The use of excess LSs is necessary because the aqueous subphase of the alveolar air-water interface (alveolar lining fluid) needs to be saturated with LSs in order to guarantee the proper operation of the surfactant adsorption-desorption process. The lungs of infants have less branching than those of adults, and therefore, the above simple volumetric scaling is inadequate when applied to adult ARDS patients, for instance, due to wall losses of liquids during bolus delivery ("coating cost"). Further, an instillation of 3-4 ml/kg of liquid to an adult ARDS patient is inadequate, because the patient's lungs are already filled with fluid. Unfortunately, clinical trials testing lower volumetric doses as expected were unsuccessful. A recent study suggested that, despite the coating cost, the 4 ml/kg dose delivers sufficient surfactant material to the alveoli of an adult ARDS patient.

A potential solution to this conundrum is aerosol delivery. However, efforts to aerosolize therapeutic LS have only met with technical difficulties. Liquid foaming is, for instance, one challenge; the typical concentration of active ingredient in a commercial LS preparation is about 25 mg/ml (Survanta), which has a high viscosity and a low surface tension, and is thus prone to foaming and swelling. Even with advancement of the nebulization technology, producing a steady stream of aerosolized LS at a high dose of 100 mg/kg without clogging the nebulization device remains challenging.

Herein we propose a solution to both the deactivation and high-dose problems. We propose a material that can function as LS by a completely different mechanism, i.e., via formation of an insoluble monolayer at the air-water interface. Such compound, being insoluble, would be resistant to deactivating effects of serum proteins because it does not desorb from the air-water interface. Also, a much lower dose would be required of such compound (est. 3.1 mg/kg) relative to current therapeutic LSs (100 mg/kg). With polymer formulations, aerosolization would be easier, too, because lower concentrations can be used. For these reasons, we think that polymers are ideal materials to be used as active ingredients in ARDS therapeutics. Polymer LSs are free of pathogenic contaminants. The most important advantage of synthetic polymer LSs over animal-derived products is mass production. If surfactant replacement therapy becomes the standard of care for ARDS treatment, the increase in demand for therapeutic LSs cannot be met by the current manufacturing method (extraction of lipid/protein active ingredients from bovine/porcine lungs). High quality polymer LSs can easily be mass-produced at lower costs.

We have developed design criteria for polymer LSs. A successful LS candidate should (1) be biocompatible/biodegradable, (2) produce an extremely low surface tension at high compression («10 mN/m) repeatedly during multiple compression-expansion cycles, (3) be resistant to serum proteins, and (4) (in the end) prove to be safe and effective in preclinical (animal) models.

In response to the unmet need, we developed polymer lung surfactants as a possible solution to these problems. Our newly-developed fully-synthetic polymer-based lung surfactants can be produced at significantly lower costs, and enable to use far simpler non-invasive non-physician-assisted aerosol delivery procedures.

Biocompatibility

Figure 3:
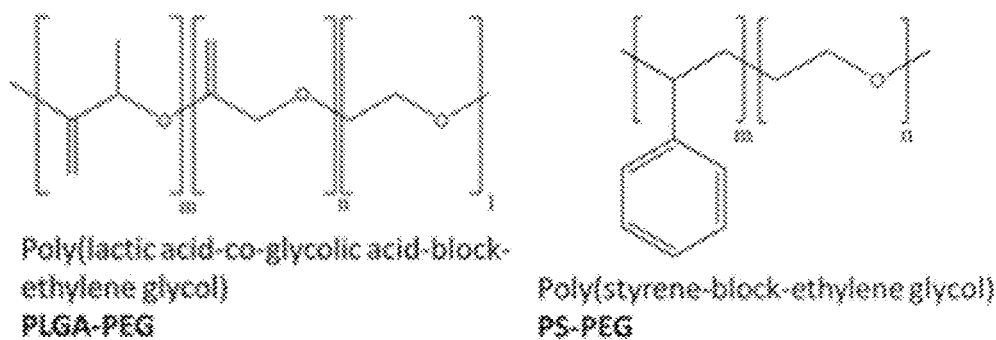
FIG. 3. Molecular characteristics of polymer LS candidate materials investigated in this study. [5,54] lactic acid:glycolic acid=47:53 by mole.

Biocompatibility is an essential prerequisite for clinical use. For this reason, our investigation has been focused on PEGylated amphiphilic block copolymers. Two examples of materials will be discussed in this article; the first is the FDA-approved biodegradable block copolymer, poly(lactic acid-co-glycolic acid-block-ethylene glycol) (PLGA-PEG), and the second is poly(styrene-block-ethylene glycol) (PS-PEG) (FIG. 3). In their micelles, the hydrophobic PLGA or PS chains form micelle core domains, and the hydrophilic PEG chains form micelle coronae. In the literature, PLGA-PEG and PS-PEG micelles have been documented to be biosafe.

For this study, monodisperse PLGA-PEG and PS-PEG micelles with well-defined sizes and shapes were prepared using the solvent exchange methodology. Although PLGA-PEG spontaneously degrades in aqueous media over a timescale of months. PS-PEG micelles were permanently stable (stable for years) at room temperature. Also, these polymer micelles did not require any pretreatment processes prior to use in order to obtain reproducible effects. Conventional lipid-based LSs typically have short shelf lives (<12 months), and require cold storage (at 2-8° C.) and/or pretreatment procedures (such as agitation and warming of the fluid) before use. This advantage in handling characteristics alone can contribute to effectively reducing the total treatment cost.

Further, micelles of PEG-based block copolymers are known to be "cyro-compatible". That is, polymeric micelles can easily be lyophilized (i.e., free-dried) and re-dispersed in aqueous solution without loss of their physico-chemical and biological characteristics. See, for instance, Logie et al., Chemistry of Materials 2014, 26(9), 2847-2855, and Moretton et al., Journal of the Royal Society Interface 2012, 9(68), 487-502. This property gives an additional advantage of the present invention in terms of increased product shelf-life and handling convenience.

Extremely Low Surface Tension (High Surface Pressure) at High Compression

The primary role of LS is to reduce work of breathing (and thus also to prevent atelectrauma) by lowering the alveolar air-water interfacial tension. A wide range of polymers have been searched and tested to identify a candidate polymer LS that produces a sufficiently low surface tension at high compression («10 mN/m). Initially, we focused our study on the FDA-approved PLGA-PEG copolymer. If spread appropriately (e.g., using chloroform as the spreading solvent), PLGA-PEG forms a well-spread film at the air-water interface, commonly referred to as a Langmuir monolayer. A Langmuir trough device was used to create an in vitro lung-mimicking test environment. When a sufficient amount of PLGA-PEG is spread on the air-water interface beyond the full coverage point, the PLGA-PEG polymers form a brush-coated insoluble film, in which the PLGA segments are anchored to the water surface (forming a slightly glassy, insoluble polymer film), and the PEG segments are submerged into the water subphase (forming a brush layer). In the highly compressed state, PLGA-PEG reduces the surface tension of water down to close to zero because of the combined effects of PLGA glass transition and PEG brush repulsion. The morphological and surface mechanical properties of Langmuir PLGA-PEG monolayers under various monolayer compression conditions are known in the art.

Figure 4:
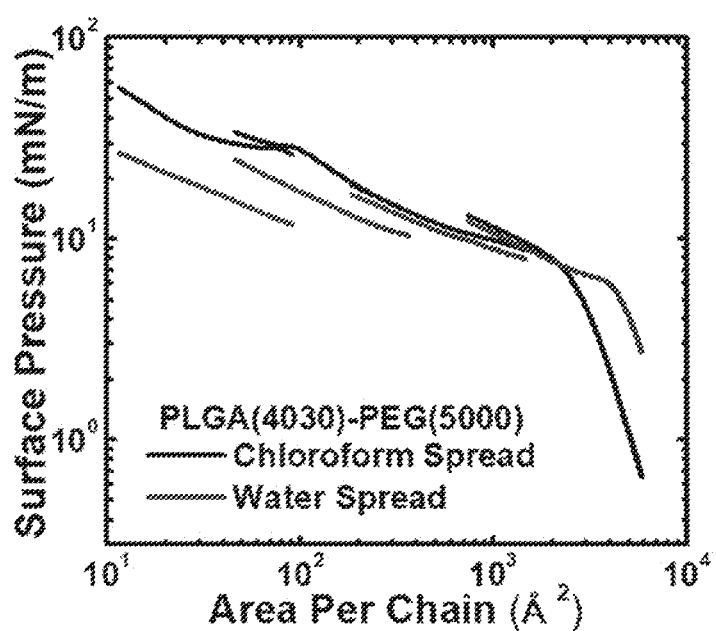
FIG. 4. Constant-compression surface pressure-area isotherms of chloroform-spread and water-spread PLGA (4030)-PEG(5000) monolayers on the surface of Milli-Q-purified water (18 MΩ·cm resistivity) at 25° C. Surface pressure was measured during compression at a rate of 3 mm/min. The mean hydrodynamic diameter of the PLGA-PEG micelles determined was 75.1±3 nm (measured by DLS). Note that the water-spread isotherms obtained in different area ranges do not overlap with each other; this indicates that the water spreading process involves significant loss of polymer to the aqueous subphase.

FIG. 4 displays the surface pressure-area isotherms obtained from Langmuir monolayers formed by PLGA (4030)-PEG(5000); the monolayers were prepared using two different spreading solvents, chloroform and water, in order to examine the influence of spreading solvent on the properties of the monolayer. Chloroform is the standard solvent for preparation of Langmuir monolayers in laboratory studies; PLGA-PEG becomes molecularly dissolved in chloroform. In real therapeutic applications, however, chloroform cannot be used as the spreading solvent. The formulation must be water-based. The aqueous PLGA-PEG spreading solution was prepared using solvent exchange. In aqueous solution, PLGA-PEG exists in the form of micelles. As shown in FIG. 4, unlike the chloroform-spread PLGA-PEG monolayer, the water-spread monolayer was unable to produce sufficiently high surface pressure (low surface tension); in the water-spread situation, the highest surface pressure observed was only about 25-30 mN/m at the highest compression level tested, which is insufficient to produce therapeutic effects.

Without being bound by any theory, it is thought that the reason why the chloroform-spread versus water-spread PLGA-PEG monolayers exhibit drastically different surface tension isotherms is due to a difference in monolayer morphology. In the chloroform-spread monolayer system, the PLGA-PEG polymers form a molecularly-spread ("anchor-brush") monolayer. In the water-spread situation, the polymers remain in the micelle state even after being spread on the water surface. PLGA-PEG micelles are highly water-compatible. So, under high compression, PLGA-PEG micelles desorb from the air-water interface and submerge into the subphase, rather than resisting to the compression (rather than producing high surface pressure). We have been experimenting with water-spread monolayers prepared from various PLGA-PEG polymers having a range of different molecular weights (3.5-28.6 kg/mol) and PEG weight fractions (28.4-74.3%). None of these samples have been observed to be able to produce sufficiently high surface pressure; even under high compression the surface pressure has never been seen to exceed about 30 mN/m.

To achieve high surface pressure, we decided to explore use of polymer micelles having stronger tendency to adsorb to the air-water interface. Specifically, we tested micelles formed by block copolymers containing more strongly hydrophobic segments such as PS-PEG micelles. Although they are both insoluble in water, PLGA and PS are very different in their levels of hydrophobicity. PS has an interfacial tension with water of $\gamma_{PS\text{-}water}$=41 mN/m, whereas PLGA has a much smaller interfacial tension with water ($\gamma_{PLGA\text{-}water}$=24.7 mN/m); PS is far more hydrophobic than PLGA. For this reason, PEG corona chains of PS-PEG micelles were expected to assume collapsed conformations, that is, in order to minimize the exposure of the hydrophobic PS domain to water. In the literature, collapsed micellar PEG brush structures have been documented for, for instance, poly(butadiene-block-ethylene glycol) (PB-PEG) micelles ($\gamma_{PB\text{-}water}$ of 45.9 mN/m). In order to confirm that PEG chains exist in a collapsed state, the mobility of the PEG brush segments of PS-PEG micelles were investigated by in situ NMR spin relaxation measurements; measurements were also performed in PLGA-PEG micelles for comparison. The longitudinal relaxation times ($T_1$) were measured by the inversion recovery method, and the transverse relaxation times ($T_2$) were measured using the Carr-Purcell-Meiboom-Gill (CPMG) spin echo sequence; $T_1$ is related to the chemical structure ("fast mode"), and $T_2$ is related to the configuration ("slow mode") of the chain segment.

Figure 5:
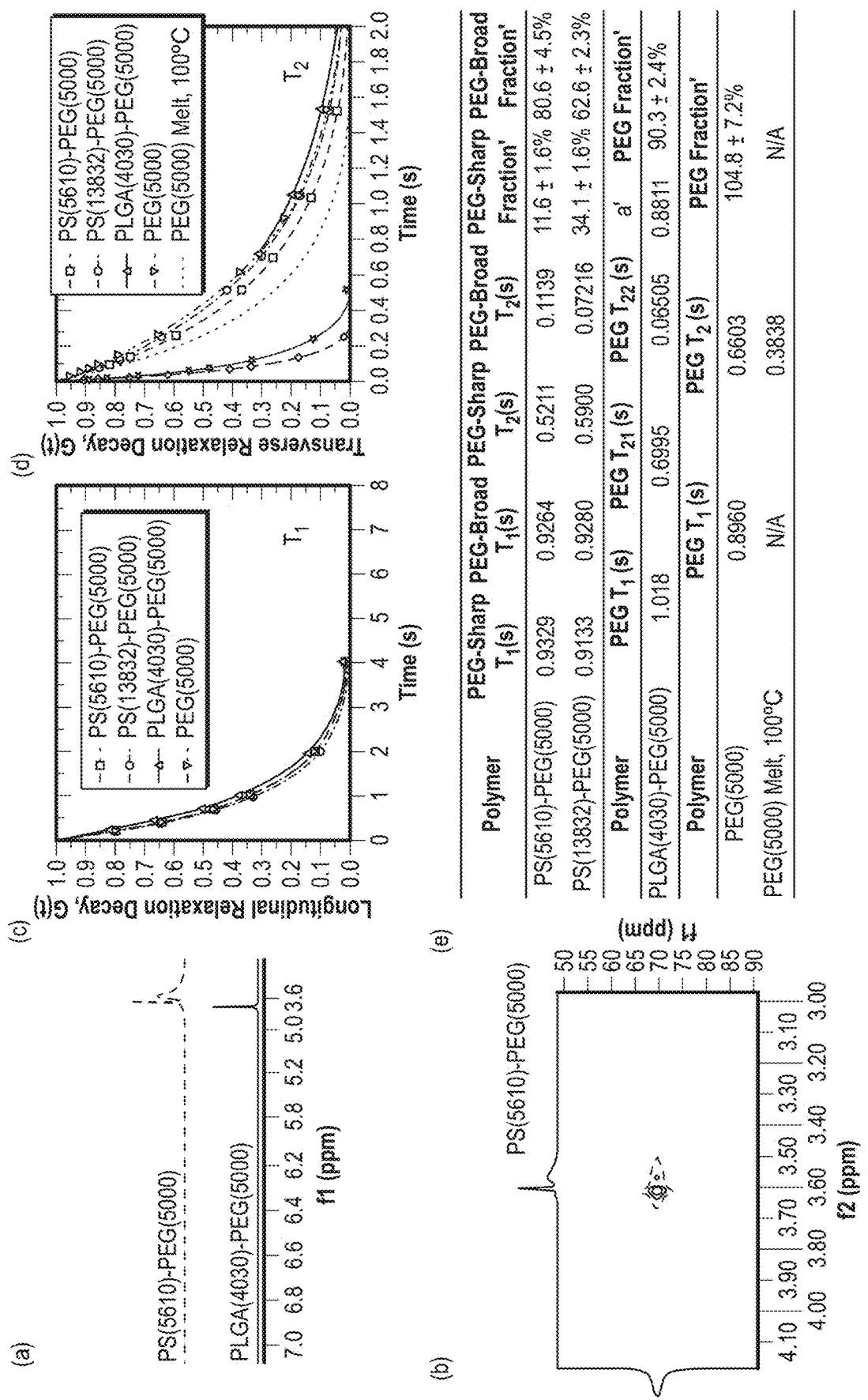
FIG. 5. (a) 1D $^1H$ NMR Spectra for PS(5610)-PEG(5000) and PLGA(4030)-PEG(5000) in $D_2O$ at 25° C. (b) 2D $^1H$—$^{13}C$ heteronuclear multiple bond correlation (HMBC) NMR Spectra for PS(5610)-PEG(5000) in D2O at 25° C. (c) Longitudinal relaxation decay curves for PEG protons at 25° C. Solid curves are fits to a mono-exponential decay function $(G(t)=\exp(-t/T_1))$. (d) Transverse relaxation decay curves for PEG protons at 25° C. As demonstrated in (a), spectra from PS(5610)-PEG(5000) and PS(13832)-PEG (5000) micelles exhibited two PEG peaks (a sharp peak at ~3.61 ppm, and a broad peak at ~3.56 ppm). The decay curves of these peaks were separately fitted with a mono-exponential decay function. Open symbols represent broad PEG peaks, and filled symbols represent sharp PEG peaks. Spectra from PEG(5000) and PLGA(2385)-PEG(5000) exhibited single PEG peaks (also demonstrated in (a)). The decay curve of PEG(5000) was fit with the mono-exponential function, and that of PLGA(4030)-PEG(5000) was fit with a bi-exponential function ($G(t)=a \cdot \exp(-t/T_{21})+(1-a) \cdot \exp(-t/T_{22})$). (e) Best fit $T_1$ and $T_2$ values. †Fractions of PEG segments contributing to the sharp and broad PEG peaks out of the total number of PEG segments available in the system, estimated based on pyridine internal reference. ‡The coefficient of the first term of the bi-exponential decay function, a. Also shown for comparison is a predicted $T_2$ value for PEG(5000) melt at 100° C. (see text).

Between PS-PEG and PLGA-PEG micelles, it is expected that the PEG $T_1$ values are identical, whereas their $T_2$ values are significantly discrepant. NMR measurements were performed on four representative systems: PS(5610)-PEG (5000), PS(13832)-PEG(5000) and PLGA(4030)-PEG (5000) micelles, and PEG(5000) homopolymers in heavy water. For PS-PEG micelles, two separate PEG proton peaks were observed (a sharp ("hydrated PEG") peak at ~3.61 ppm, and a broad ("collapsed PEG") peak at ~3.56 ppm) (FIG. 5(a)); the NMR spectra of PLGA-PEG micelles (and PEG homopolymers) exhibited only one sharp peak of hydrated PEG at ~3.63 ppm (FIG. 5(a)). The 2D $^1$H—$^{13}$C heteronuclear multiple bond correlation (HMBC) NMR Spectra (FIG. 5(b)) confirmed that the two peaks in the PS-PEG spectra were not due to impurities. These two peaks were separately analyzed for $T_1$ and $T_2$. The results are displayed in FIGS. 5(c) and 5(d).

As shown in FIG. 5(c), all four samples (PS(5610)-PEG (5000), PS(13832)-PEG(5000) and PLGA(4030)-PEG (5000), and PEG(5000)) exhibited an identical PEG $T_1$ value (0.91±0.03 s), which confirms the validity of the measurements. To the contrary, the measured PEG $T_2$ values varied significantly from sample to sample. To provide a scale of the PEG mobility, the $T_2$ value for 5 kg/mol PEG homopolymer melt at 100° C. was calculated; at this condition, PEG has a Rouse time of 281.52 ps, which translates to $T_2$=0.3838 s. Hydrated PEG chains are expected to have longer $T_2$ values than 0.3838 s, because of their higher mobility. The $T_2$ value for hydrated free PEG(5000) chains was estimated to be 0.6604 s from a fitting of the transverse decay curve to a mono-exponential function, G(t)=exp(-t/$T_2$). The transverse decay curve of PLGA(4030)-PEG(5000) micelles was fit better with a bi-exponential function, G(t) =a·exp(-t/$T_{21}$)+(1-a)·exp(-t/$T_{22}$), because the mobility of PEG segments vary depending on the proximity of the PEG segment to the grafting surface. $T_{21}$ corresponded to PEG segments distant from the grafting surface, which were largely responsible for the overall signal intensity (a=0.8811). $T_{22}$ corresponded to PEG segments close to the grafting surface. The $T_{21}$ value of PLGA-PEG micelles was higher than that of PEG melt and slightly lower than that of hydrated PEG(5000), which indicates that the PEG corona chains of PLGA-PEG micelles were indeed fully hydrated.

For PS-PEG micelles, NMR spectra exhibited two separate PEG peaks (as demonstrated in FIG. 5(a)). These two PEG peaks were separately fit with a mono-exponential function. The $T_2$ values obtained from the decay curves of the sharp PEG peaks of PS-PEG micelles were comparable to the $T_{21}$ value obtained from PLGA-PEG micelles, which suggests that the sharp PEG peaks corresponds to the hydrated PEG segments of PS-PEG micelles. However, the $T_2$ values obtained from the broad PEG peaks of PS-PEG micelles were very small, even smaller than the $T_2$ value obtained from PEG melt, which unambiguously indicates that, in PS-PEG micelles, substantial portions of PEG segments existed in a collapsed state (because of the strong hydrophobicity of the PS material).

Further, it is very interesting to note that PS(13832)-PEG (5000) micelles has a higher fraction of hydrated PEG segments compared to PS(5610)-PEG(5000) micelles. The absolute concentrations of hydrated vs. collapsed PEG segments of PS-PEG micelles could be determined using an NMR signal from pyridine added as an internal standard. PS(13832)-PEG(5000) micelles were found to have a significantly higher proportion of hydrated PEG segment (34.1±1.6%) than PS(5610)-PEG(5000) micelles (11.6±1.6%) (see the table at the bottom of FIG. 5). These results clearly support that (for some reason that is yet unclear) PS(13832)-PEG(5000) micelles are less hydrophobic (i.e., contain more hydrated PEG segments) than PS(5610)-PEG(5000) micelles and therefore expected to be less strongly bound to the air-water interface.

Figure 6:
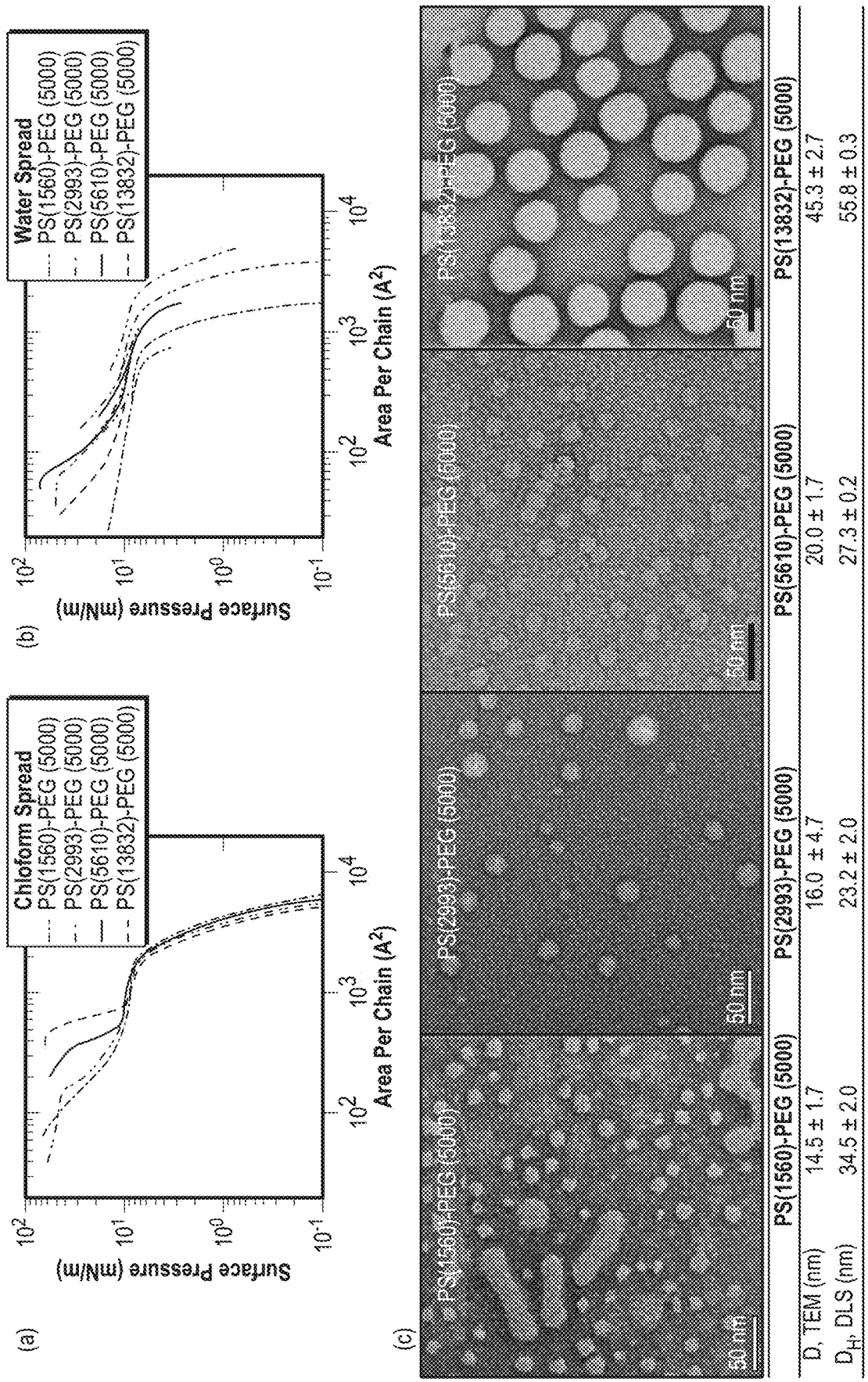
FIG. 6. Constant-compression surface pressure-area isotherms of (a) chloroform-spread and (b) water-spread monolayers of four different PS-PEG materials at 25° C. Milli-Q-purified water (18 MΩ·cm resistivity) was used as the subphase. The monolayer compression rate was 3 mm/min. (c) TEM images of PS-PEG micelles formed in bulk water solutions. The dried micelle samples were negatively stained with uranyl acetate. Summarized in the table at the bottom are diameters of PS-PEG micelles as determined by TEM or DLS. †Excluding elongated micelles.

In the literature, in fact, it has been documented that surface micelles formed by spreading a PS-PEG solution in chloroform onto the water surface typically exhibit high surface pressure (>60 mN/m) at high compression. Chloroform-spread PS-PEG surface micelles are anisotropic in molecular morphology because of the asymmetry of the air-water interface; in bulk water solution, isotropic (or axisymmetric, to be more exact) micelle morphologies are typically obtained (FIG. 6(c)). This morphological difference might produce a difference in the surface pressure-area isotherm. Prior to this investigation, it was unknown whether water-spread PS-PEG micelle monolayers would be able to produce similar high surface pressure as required for use in LS therapeutic applications. The surface pressure-area isotherms were measured for four different PS-PEG materials, PS(1560)-PEG(5000), PS(2993)-PEG(5000), PS(5610)-PEG(5000), and PS(13832)-PEG(5000) (both chloroform-spread and water-spread). The data are presented in FIGS. 6(a) and 6(b). For constructing a full surface pressure-area isotherm curve over a large range of monolayer area, it was necessary to perform multiple (2 to 3) measurements in different ranges of areas because of the size limitation of the Langmuir trough. Interestingly, the isotherms obtained from chloroform-spread monolayers over different areas superimposed closely on one another without breaking (FIG. 6(a)), which suggests that when the polymers were spread from chloroform solutions, the loss of material to the subphase was negligible. On the other hand, as shown in FIG. 6(b), the curves from different areas for water-spread monolayers were disjointed, which suggests that the water-spreading procedure caused some loss of material (PS-PEG micelles) to the subphase. This trend is consistent with what was observed in experiments with PLGA-PEG (FIG. 4).

Chloroform-spread PS-PEG monolayers exhibited similar isotherm profiles at surface pressures «10 mN/m, regardless of the PS block molecular weight (FIG. 6(a)). When compressed beyond the 10 mN/m surface pressure level, higher PS block molecular weights produced steeper rises in surface pressure for the chloroform-spread monolayers (FIG. 6(a)). We suspect that this observation is due to the fact that higher molecular weight PS segments result in larger-sized core domains for the PS-PEG surface micelles. Unlike the chloroform-spread cases, the surface pressures of water-spread PS-PEG monolayers did not exhibit a monotonic trend with respect to the PS block molecular weight. One notable observation was that in water-spread systems, maximum surface pressure was achieved at an intermediate PS block molecular weight; the steepest rise of surface pressure during compression was observed with the water-spread PS(5610)-PEG(5000) micelle monolayer (FIG. 6(b)). Interestingly, the water-spread PS(13832)-PEG(5000) monolayer exhibited the lowest maximum surface pressure among all systems tested (FIG. 6(b)). The maximum surface pressure of water-spread PS(13832)-PEG(5000) (10-20 mN/m) was comparable to those of water-spread PLGA-PEG micelles. These results are consistent with the above NMR results that water-spread PS(13832)-PEG(5000) micelles have a higher proportion of hydrated PEG segments (34.1±1.6%) than water-spread PS(5610)-PEG(5000) micelles (11.6±1.6%). These results suggest that the proper molecular parameters (e.g., PS molecular weight relative to PEG molecular weight) need to be carefully chosen to satisfy the high surface pressure requirement for use in surfactant replacement therapy.

Overall, our investigation has now led to an identification of a promising class of candidate materials that have the desired surface tension/pressure properties for potential LS applications: the PS(5610)-PEG(5000) block copolymer formulated in the form of aqueous micelles. Aqueous micelle solutions of PS(5610)-PEG(5000) exhibit excellent colloidal stability over a long period of time; a PS(5610)-PEG(5000) micelle sample was confirmed to reproduce the same surface pressure-area profile after being stored at room temperature for at least over 3 months.

Protein Resistance, Safety and Efficacy

In ARDS, respiratory failure (atelectasis/de-recruitment of the alveoli) is aggravated due to deactivated LSs caused by an increase level of surface active deactivating agents such as serum proteins. Therapeutics developed for treatment of NRDS are not effective in treating adult ARDS, because of the deactivation of injected LSs. The protein resistance characteristics of PS(4418)-PEG(5000) micelle LSs were evaluated; PS(4418)-PEG(5000) forms stable micelles of 47.3±1.2 nm hydrodynamic diameter in water, and produces high surface pressure (close to 70 mN/m) under high compression similarly to PS(5610)-PEG(5000). A commercial LS, Infasurf (ONY), was used as control; Infasurf has been known to have the highest therapeutic effect for NRDS treatment.

The main reason why current surfactant therapeutic formulations for NRDS (animal-extracted lipid/protein formulations such as Infasurf, Survanta, and Curosurf) are not effective in treating adult ARDS is the surfactant deactivation caused by deactivating agents (e.g., serum proteins). In this study, we first tested how Infasurf responds to an addition of a surface active protein, bovine serum albumin (BSA). As shown in FIG. 7(a), BSA deactivated Infasurf. Upon addition of BSA, Infasurf lost its capability to increase the surface pressure above 60 mN/m; the maximum surface pressure decreased (from about 65 mN/m) down to about 28 mN/m. BSA also has a similar effect on Survanta (data not shown). To the contrary, the surface activity of PS-PEG micelles was largely unaffected by added BSA (FIG. 7(b)).

Safety of Intratracheally Injected PS-PEG Micelles in Adult Mice

A preliminary study was performed to evaluate the safety of intratracheally administered PS-PEG lung surfactants in adult mice (normal BALB/c, 7 weeks old, female). Three polymer dose levels were tested: 0.64, 6.5 and 64 mg polymer per kg mouse body weight (20 microliters of 0.6, 6 and 60 mg/ml PS-PEG micelle solutions were respectively injected to mice). The polymer used was PS(4418)-PEG (5000); the overall molecular weight and block composition were selected based on in vitro results discussed earlier. Separate experiments were conducted to confirm that this PS(4418)-PEG(5000) material satisfied four polymer lung surfactant performance criteria discussed earlier. Polymer lung surfactants were injected through surgical incision in the trachea. Mice were monitored for indications of toxicity (weight loss and behavioral symptoms) for 14 days since the time of injection.

Figure 8:
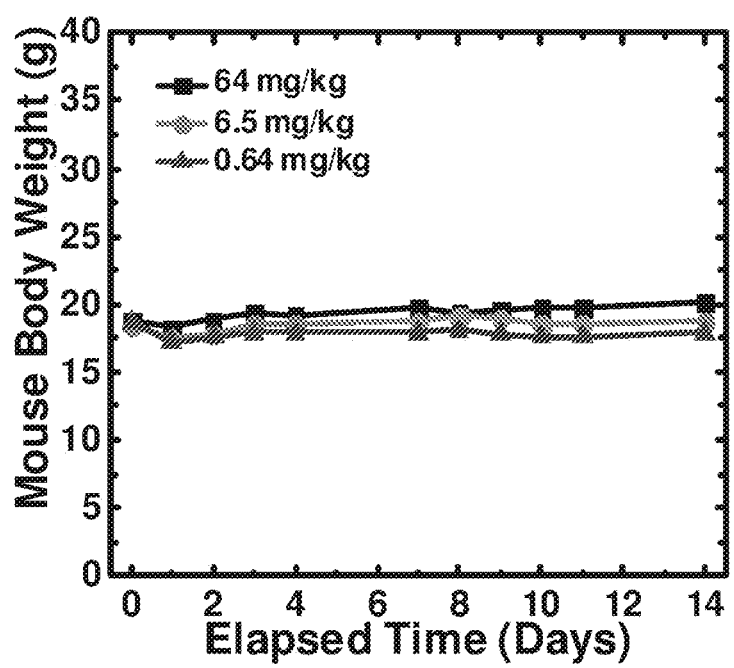
FIG. 8. Mouse body weight measured as a function of time following intratracheal injection of different doses of PS(4418)-PEG(5000) micelle polymer lung surfactants. Each dose group consists of one mouse.
Figure 9:
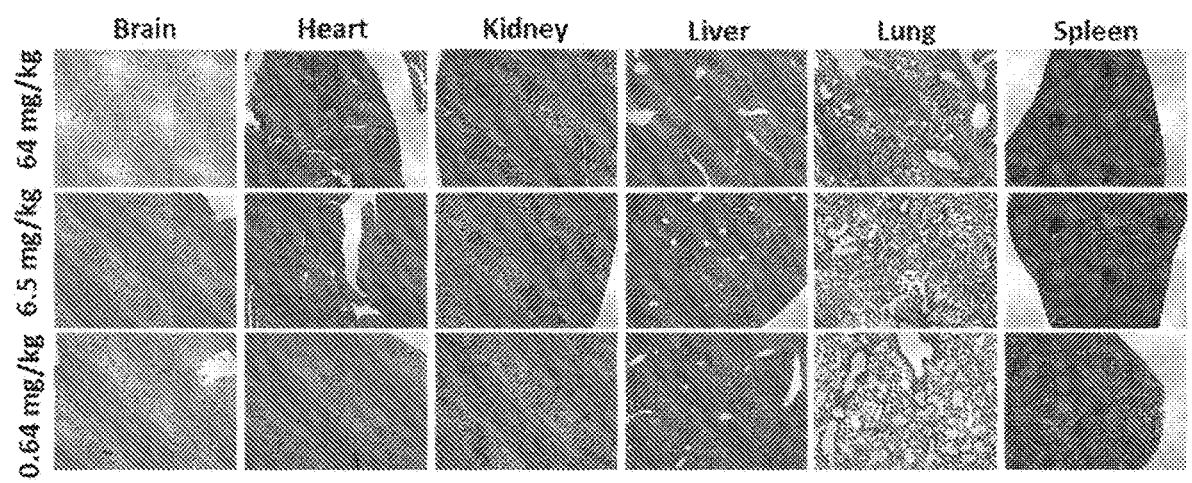
FIG. 9. H&E-stained histological sections (1600 μm×1200 μm) of mouse organs taken at 2 weeks after intratracheal injection of 1.6 mg PS(4418)-PEG(5000) micelle polymer lung surfactants.

Mouse body weights are presented in FIG. 8. The initial weight loss observed during the first 1 or 2 days is perhaps due to the surgical incision. Once mice recovered from the surgery, they exhibited normal behavior and started steadily gaining body weight. At all polymer doses tested, no signs of toxicity was observed in mice during the 14 day period. At day 14 post injection, mice were sacrificed, and major organs (brain, heart, kidney, liver, lung, and spleen) were collected for histological analysis. A blinded histopathological evaluation of H&E-stained organ specimens was performed by a histopathology expert, who confirmed that all organs were normal; representative images of the H&E-stained tissue sections are presented in FIG. 9.

Efficacy of Intratracheally Injected PS-PEG Micelles in Preterm Rabbit Lungs

Pressure-volume (PV) measurements using ex vivo lung models (excised animal lungs) are a common method of evaluating the efficacy of an RDS therapeutic. Due to the high reproducibility of lung PV mechanics among independent tests, ex vivo PV testing is an FDA-approved method for quality control(QC)/quality assurance(QA) of animal-extracted lung surfactant products.[2] The animal model used in this study was preterm 27-day gestation New Zealand White Rabbit fetuses. A commercial bovine-extracted lung surfactant product, Newfacten (Yuhan Corporation) was also tested as positive control.

The same polymer used in the in vivo toxicity study in mice, PS(4418)-PEG(5000), was also used in the present ex vivo efficacy study in rabbit fetuses. Three different polymer doses were used: (0,) 6, 60 and 96 mg polymer per kg rabbit fetal body weight, achieved by injecting 1.5 ml per kg body weight of 0.6, 6 and 60 mg/ml PS-PEG micelle solutions, respectively, to rabbit fetus lungs (the rabbit fetuses weighed between 20 and 30 g); 96 mg/kg was the maximum possible dose achievable with a polymer concentration of 64 mg/ml (which is the highest polymer concentration achievable with our current solvent exchange procedure) at the optimal liquid installation volume of 1.5 ml per kg body weight.

Figure 10:
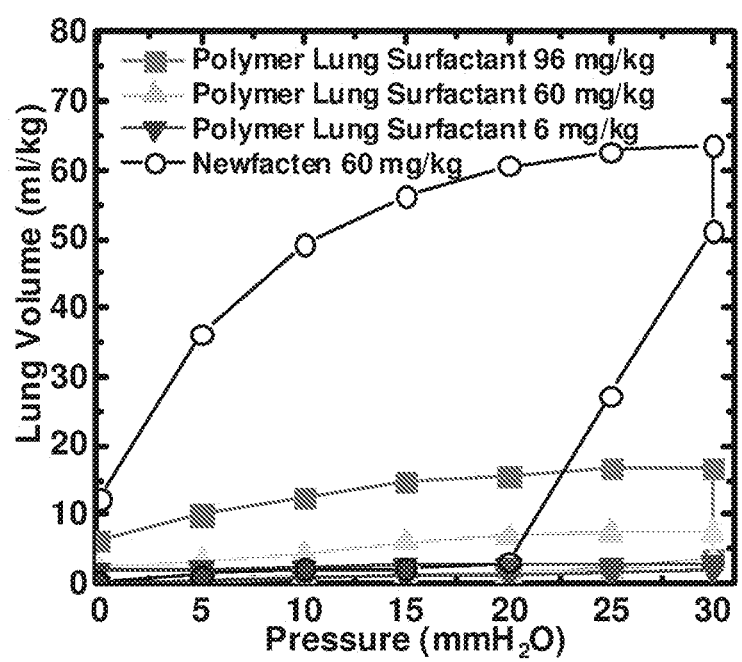
FIG. 10. Ex vivo pressure-volume (PV) lung mechanics of 27-day gestation rabbit fetus lungs following injection of various doses of PS(4418)-PEG(5000) lung surfactants. Each group consisted of five rabbit fetuses.

The PV profiles of rabbit fetus lungs following PS-PEG (or Newfactan) injection are displayed in FIG. 10. At a glance, it appears that PS-PEG lung surfactants exhibit a lower efficiency in increasing the lung compliance and thus reducing the respiratory work than the commercial formulation, Newfactan, at an identical mass dose. However, these results are promising in that they demonstrate dose-dependent effects of PS-PEG on improving lung compliance. Further, the slope of the PS-PEG dose dependence trend suggests that PS-PEG indeed has great potential for use in RDS therapy at its optimal dose. Consequently, further study is needed to identify the optimal dose of PS(4418)-PEG (5000) required for sufficient therapeutic effect.

Figure 11:
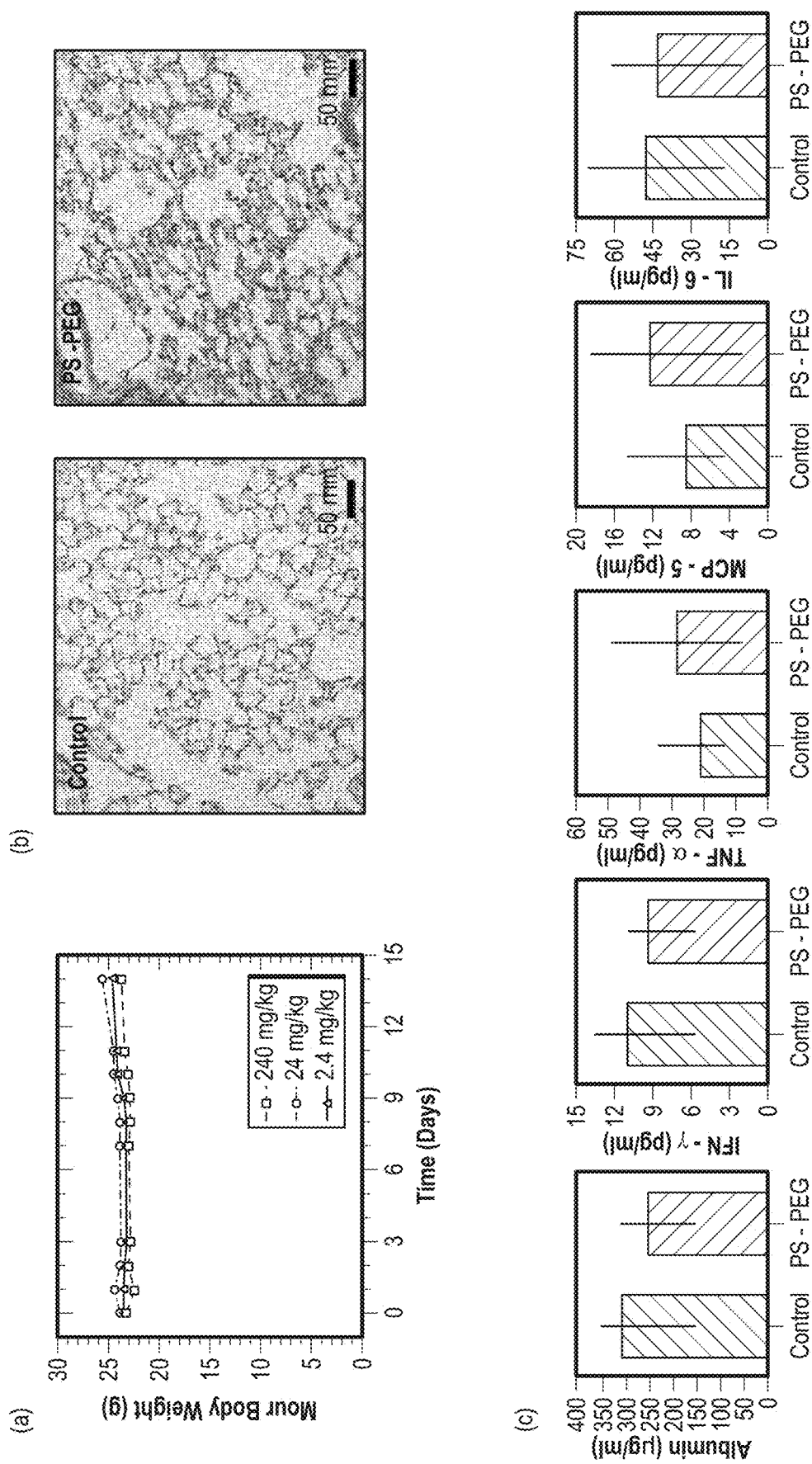
FIG. 11(a) Mouse body weights recorded as a function of time following intratracheal instillation of different doses of PS(4418)-PEG(5000) micelles at Day 0 (N=1). (b) A representative H&E-stained histological section of the lungs taken at 7 days after intratracheal injection of 240 mg PS(4418)-PEG(5000) micelles per kg body weight in mice (N=1). (c) Levels of albumin and 4 different cytokines in BAL fluids collected from mice at 7 days after intratracheal injection of 240 mg/kg PS(4418)-PEG(5000) micelles. BAL fluids from untreated mice were used as control. Measurements were performed in quadruplicates (N=4). Error bars represent standard deviations.

Safety and Efficacy of Intratracheally Injected PS-PEG Micelles in a Mouse ARDS Model of Acid Aspiration The safety and efficacy of the PS(4418)-PEG(5000) micelle LS were evaluated in vivo in C57/BL6 mice (8-12 weeks old, female). The PS(4418)-PEG(5000) micelle solution became highly viscous (i.e., non-Newtonian) at polymer concentrations greater than about 6 wt. % (60 mg/ml). A maximum tolerated dose (MTD) study was performed again using an improved procedure. In this MTD study, the effects of three PS(4418)-PEG(5000) dose levels (2.4, 24, 240 mg of polymer per kg of mouse body weight) were studied (N=1); fixed volumes of polymer solutions (4 ml per kg mouse body weight) at 3 different polymer concentrations (0.6. 6, and 60 mg/ml) were administered into mice via non-surgical intratracheal instillation (4 ml/kg represents the maximum tolerated volume for an intratracheal injection of a liquid that does not cause injury or blockage in the lungs of a mouse). Following polymer instillation, mice were monitored for symptoms of toxicity (weight loss, and behavior change) for 14 days. The body weight profiles are presented in FIG. 11(a). At all dose levels, no signs of toxicity were observed for the 14-day period. The MTD of PS(4418)-PEG(5000) micelles is greater than 240 mg/kg. Further dose escalation was not attempted, because 240 mg/kg already far exceeds the therapeutic dose (as will be discussed later).

Toxicological analysis was performed on the lungs of mice instilled with PS(4418)-PEG(5000) micelles at the 240 mg/kg dose level; lung histology slides (N=1) and broncho-alveolar lavage (BAL) fluids (N=4) were collected at 7 days post injection. A representative H&E-stained histological section of the lungs is presented in FIG. 11(b). No histopathological changes were detected in the lungs treated with PS(4418)-PEG(5000) micelles relative to the untreated control. BAL fluids were analyzed for levels of albumin (to detect permeability injury) and cytokines that reflect inflammation (IFN-γ, TNF-α, MCP-5, and IL-6). The results are presented in FIG. 11(c). As shown in the figure, the levels of these five markers were not significantly different between baseline assessment and 240 mg/kg PS(4418)-PEG(5000) treatment, confirming the safety of this treatment.

Figure 12:
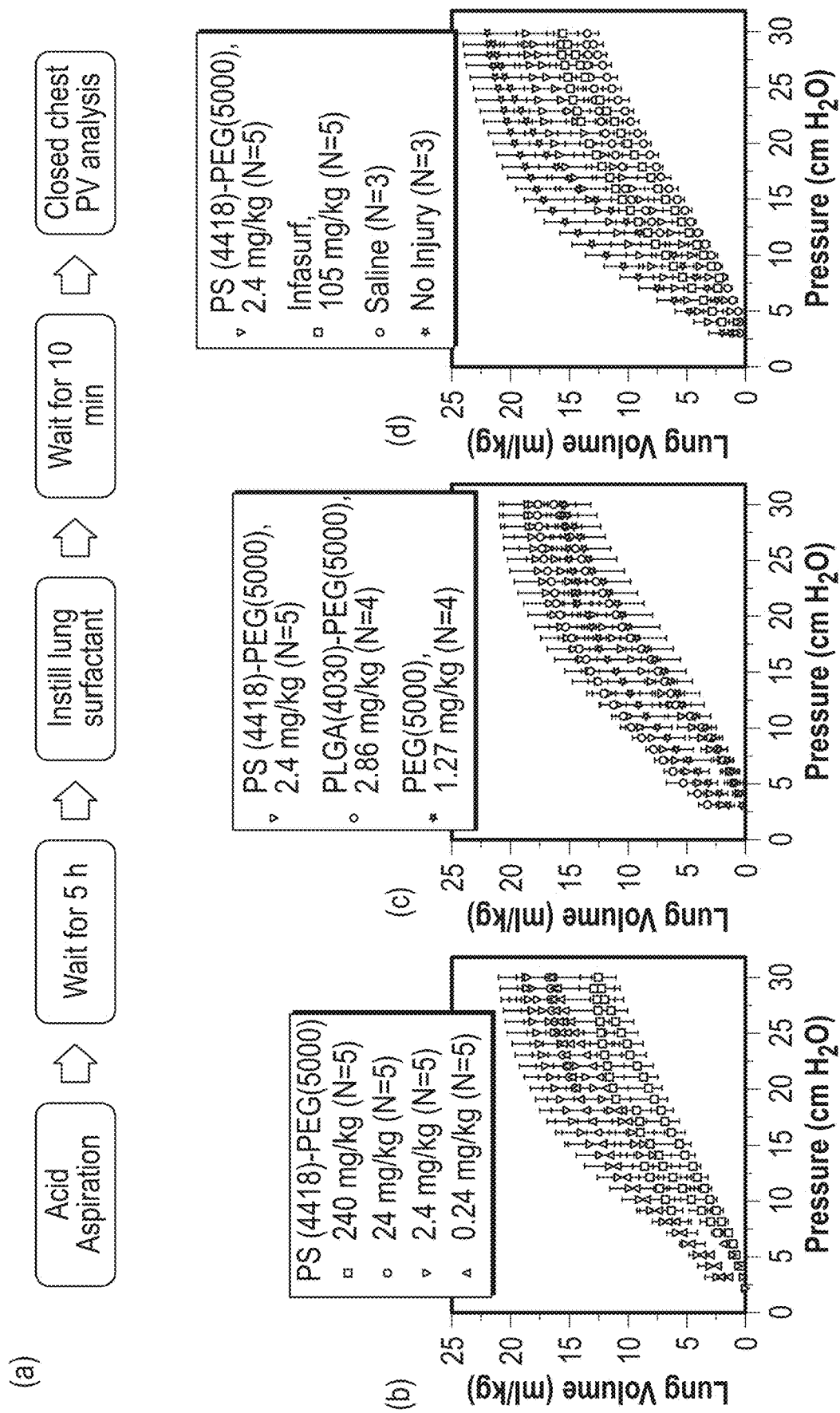
FIG. 12. (a) Diagrammatic description of the procedures used in LS efficacy tests using acid aspiration lung injury ARDS mouse models. (b) Closed chest pressure-volume (PV) curves of acid-injured mouse lungs following intratracheal instillation of PS(4418)-PEG(5000) micelles at four different polymer doses. (c) Closed chest PV curves of acid-injured mouse lungs following intratracheal instillation of PS(4418)-PEG(5000) micelles (0.6 mg/ml×4 ml/kg), PLGA(4030)-PEG(5000) micelles (0.714 mg/ml×4 ml/kg) or PEG(5000) homopolymers (0.3185 mg/ml×4 ml/kg). (d) Closed chest PV curves of acid-injured mouse lungs following intratracheal instillation of PS(4418)-PEG(5000) (0.6 mg/ml×4 ml/kg), Infasurf (35 mg/ml×3 ml/kg) or saline (4 mag). Also included is the curve from non-injured mice (No Injury). Error bars represent standard deviations.

The efficacies of polymer LSs were tested in a mouse model of acid aspiration-induced lung injury. Quasi-static closed chest pressure-volume (PV) measurements were used to determine the level of lung injury. FIG. 12(a) presents a schematic representation of the overall test procedure. Deactivation of LS due to lung injury causes a downward shift of the PV relationship (because of the reduced compliance of the lungs), whereas a successful treatment with therapeutic LS would shift the PV curve upward (because of the recovered compliance of the lungs); see FIG. 12(d). First, to determine the optimal therapeutic dose for PS(4418)-PEG (5000), closed chest PV tests were performed at four different polymer doses: 0.24, 2.4, 24 and 240 mg polymer per kg body weight. As shown in FIG. 12(b), the highest efficacy (the greatest upward shift of the PV curve) was obtained at 2.4 mg PS(4418)-PEG(5000)/kg. This optimal dose value is quite consistent with the theoretical amount of surfactant material needed to coat the whole surface area of the lungs (≈3.1 mg/kg), which supports that PS(4418)-PEG(5000) micelles indeed form an insoluble monolayer at the alveolar air-water interface. At lower doses, polymer's efficacy is lower because the absolute amount of polymer available is insufficient to cover the whole air-water interface. However, the lower efficacy seen at higher polymer doses was unexpected; it appears that higher doses of PS(4418)-PEG(5000) produced adverse biological effects in acid-injured lungs. The exact origin of this behavior require further study.

To validate whether the efficacy of PS(4418)-PEG(5000) micelles indeed originates from their strong tendency adsorb to the air-water interface, quasi-static closed chest PV tests were also performed on less surface active compounds, PLGA(4030)-PEG(5000) micelles and PEG(5000) homopolymers; water-spread PLGA-PEG micelles and PEG homopolymers are normally unable to produce high surface pressure because they are prone to desorb from the air-water interface under high compression. For comparison with PS(4418)-PEG(5000) micelles at 2.4 mg/kg, a dose level of 2.86 mg/kg was used for PLGA(4030)-PEG(5000) micelles, and a dose level of 1.27 mg/kg for PEG(5000) homopolymers, which gave the same PEG dose value (1.27 mg/kg) for all three systems. The results displayed in FIG. 12(c) strongly support that in vivo therapeutic efficacy clearly correlates with high surface pressure generating capability.

Figure 7:
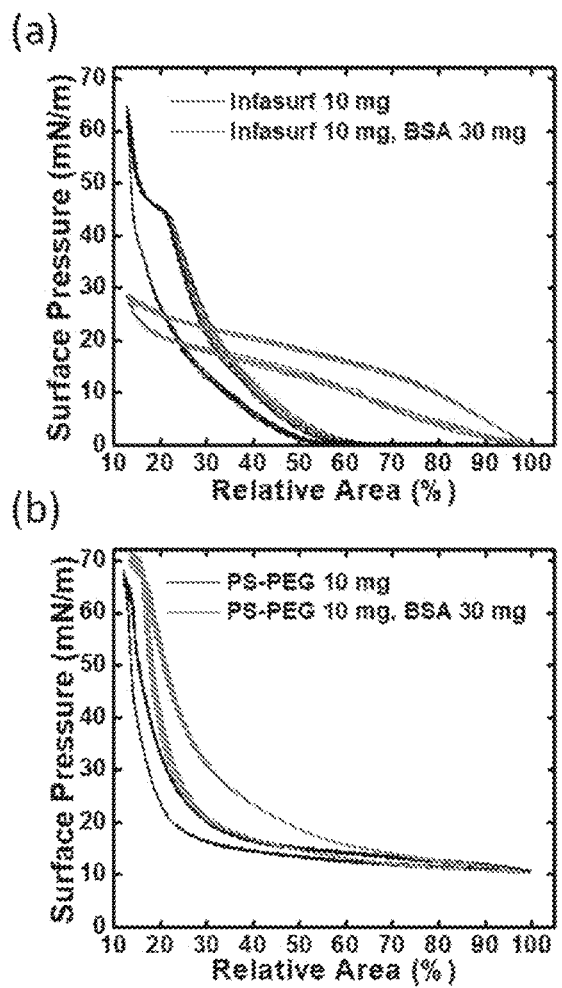
FIG. 7. Surface pressure-area isotherms for (a) Infasurf (4 mg) with and without the addition of BSA (30 mg), and (b) water spread PS(4418)-PEG(5000) (10 mg) with and without the addition of BSA (30 mg) during repeated compression-expansion cycles. A typical experiment was performed as follows: (1) Infasurf or PS(4418)-PEG(5000) was water-spread on water; (2) 30 minutes were waited for equilibration; (3) BSA was injected into the subphase without perturbing the Infasurf or PS(4418)-PEG(5000) interface; (4) compression-expansion cycles were initiated following a 10-minute waiting period. The data displayed represent the last 10 compression-expansion cycles of a total 50 continuous cycles performed after spreading Infasurf or PS-PEG micelles. The subphase solution used contained 150 mM NaCl, 2 mM $CaCl_2$ and 0.2 mM $NaHCO_3$ (pH 7.0-7.4, 25° C.). The monolayer was compressed/expanded at a rate of 50 mm/min; one compression-expansion cycle took 7.18 minutes. At the "100% relative area", 4 mg of Infasurf or PS(4810)-PEG(5000) was spread on water in a Langmuir trough with 780 $cm^2$ surface area and 1.4 L subphase volume; "100% relative areas" corresponded to 0.972 and 12.2 $Å^2$/molecule for Infasurf and PS(4810)-PEG(5000), respectively.

In order to demonstrate the role of protein resistance in producing efficacy in treating ARDS, FIG. 12(d) compares closed chest PV curves for protein-resistant PS(4418)-PEG (5000) micelles and a protein-deactivatable commercial NRDS LS, Infasurf; see FIG. 7 for effects of serum proteins on the air-water interfacial activities of these compounds. For Infasurf, closed chest PV tests were performed using a dose level of 105 mg/kg (=35 mg/ml concentration×3 ml/kg dose volume). In previous clinical testing of Infasurf in adult ARDS patients, an insufficient dose (=60 mg/ml×1 ml/kg) has been used; the study failed to demonstrate therapeutic benefits. In a different clinical trial involving pediatric ARDS patients, a higher Infasurf dose (=35 mg/ml×3 ml/kg) was tested, which resulted in an improved treatment outcome; the lungs of adult mice are known to be physiologically closer to the lungs of pediatric patients than those of adults. For this reason, we chose the 105 mg/kg dose for Infasurf. As shown in FIG. 12(d), protein-resistant PS(4418)-PEG(5000) micelles indeed produce greater recovery of acid-injured lungs than protein-sensitive Infasurf. It should be noted that the dose level used for PS(4418)-PEG(5000) micelles was equal to only about 2.3% of that used for Infasurf. In a previous clinical trial testing aerosolized Exosurf for treatment of ARDS, the unsuccessful outcome has been attributed to low efficiency of delivery; only less than 4.5% of injected dose (<5 mg out of 112 mg aerosolized DPPC per kg per day) reached the deep lungs. The significantly lower amount of polymer needed to produce therapeutic effect might serve as an enabling factor for aerosol delivery of the formulation to the lung.

Our data suggest that polymer LSs have great potential for use in ARDS therapy. Since the initial development of animal-derived NRDS therapeutics in 1980s, little further progress has been achieved in this field. Aerosol delivery and synthetic protein replacement have been the main thrust in research, but efforts have met with limited success. Testing fully synthetic polymer materials for ARDS/NRDS treatments represents a radical shift in the direction of LS research. Polymer LSs may open the door to new therapeutic options for the treatment of ARDS that had not previously been feasible with conventional lipid-based NRDS therapeutics.

For the first time, the concept of using a completely synthetic polymer material as an active ingredient in ARDS/NRDS therapeutics is proposed, and its safety and feasibility has been demonstrated. Polymer LS has the potential to address the limitations of current animal-derived lipid-based NRDS therapeutics: high production/treatment costs, limited supply, and complex delivery procedures. Polymer LSs have far longer shelf lives, and would not require any complicated pretreatment processes prior to use in treatment. Unlike lipid-based LSs, the dynamic surface active characteristics of polymer LSs do not degrade even in the presence of completing surface active proteins. In preliminary animal studies it was confirmed that intratracheally-administered polymer LSs can be tolerated (and cleared from the body) without causing damage in major organs in mice, and are capable of producing dose-dependent effects on improving the compliance of acid-injured mouse lungs in vivo. Further research is warranted to optimize the formulation for maximum therapeutic effect and to evaluate the detailed short- and long-term toxicology of the material.

EXPERIMENTAL PROCEDURES

PLGA-PEG and PLGACL-PEG Synthesis

PLGA-PEG and PLGACL-PEG materials were synthesized by ring-opening polymerization using a tin catalyst. Purified poly(ethylene glycol) monomethyl ether (PEG-OH, $M_n$=5,000 g/mol, Sigma Aldrich) was used as the macroinitiator, and tin(II) 2-ethylhexanoate (Sigma Aldrich) was used as the catalyst. The polymerization reactions were run at 130° C. The D,L-lactide (Lactel) and glycolide (Sigma Aldrich) monomers were twice recrystallized from toluene (Sigma Aldrich) and tetrahydrofuran (Sigma Alrdich) prior to use. The ε-caprolactone (Sigma Aldrich) monomer was used as received. The synthesized PLGA-PEG and PLGACL-PEG products were precipitated in 2-propanol (Sigma Aldrich) and dried under vacuum before use/storage at refrigeration temperatures.

PS-PEG Synthesis

PS-PEG materials were synthesized by Reversible Addition-Fragmentation Chain-Transfer (RAFT) polymerization. 4-cyano-4-[(dodecylsulfanylthiocarbonyl) sulfanyl] pentanoic acid (Sigma Aldrich) was used as the RAFT agent. First, the RAFT agent was conjugated to purified poly (ethylene glycol) monomethyl ether (PEG-OH, $M_n$=5,000 g/mol, Sigma Aldrich) by Steglich esterification.[52] The PEG-OH (1 g, 0.2 mmol), the RAFT agent (161.4 mg, 0.4 mmol), and 4-dimethylaminopyridine (Sigma Aldrich, 4.89 mg, 0.04 mmol) were mixed in 10 ml dichloromethane (Sigma Aldrich), and was kept under magnetic stirring at 0° C. A separately prepared dicyclohexylcarbodiimide (82.5 mg, 0.4 mmol) solution in dichloromethane (5 ml) was drop-wise added to the above mixture, and was allowed to undergo reaction for 5 minutes at 0° C. and then for 3 hours at 20° C. to produce "PEG-RAFT". The as-synthesized PEG-RAFT product was first filtered through filter paper to remove the insoluble urea byproduct, and was then further purified by precipitation in hexane twice. The RAFT polymerization reaction was performed at 70° C. by mixing the PEG-RAFT, inhibitor-free styrene (Sigma-Aldrich), and a free radical initiator, azobisisobutyronitrile (Sigma-Aldrich) in dioxane (Sigma Aldrich). The resulting PS-PEG products were precipitated twice in hexane, and dried under vacuum.

Polymer Characterizations

The number averaged molecular weights ($M_n$) of the polymers were determined by $^1$H NMR spectroscopy using a Bruker ARX NMR spectrometer (500 MHz). For $^1$H NMR measurements, polymer samples were prepared in deuterated chloroform at a polymer concentration of 5 wt. %. The polydispersity indices (PDIs) of the polymers were measured by size-exclusion chromatography (SEC) using an Agilent Technologies 12000 Series instrument equipped with a Hewlett-Packard G1362A refractive index detector and three PLgel 5 μm MIXED-C columns. Tetrahydrofuran was used as the mobile phase (kept at 35° C., flowing at a rate of 1 ml/min). Calibration was performed using polystyrene standards (Agilent Easi Cal).

Surface Pressure-Area Isotherms

The surface tension-area isotherms for Infasurf, Survanta and polymer LSs were measured using a KSV 5000 Langmuir trough (51 cm×15 cm) with double symmetric barriers. The total surface area of the trough was 780 cm², and the subphase volume was 1.4 L. Filter paper Wilhemly probe was used for surface tension measurements. Before each measurement run, the trough and the barriers were cleaned three times using ethanol and Milli-Q-purified water. The surface of water was also aspirated to remove any surface active contaminants. When the water surface was completely clean, the surface tension reading did not change during a blank compression run. LS samples were spread onto water using a Hamilton microsyringe, i.e., by forming a microliter-sized droplet at the tip of the syringe needle and letting it contact the water surface. The Langmuir trough was used to create a system that mimics the air-water interface of the alveolus. However, it should be noted that only qualitative connections can be established between the actual breathing process (e.g., FIG. 2(*a*)) and the Langmuir trough experiment (FIG. 2(*b*)) because of the differences in such parameters as compression/expansion rate, surface area to volume ratio, interfacial curvature, etc.

Polymer Micelle Preparation

The solvent exchange procedure was used to prepare spherical polymer micelles. 200 mg of the polymer was first dissolved in 4 ml of acetone (Sigma Aldrich). Then 36 ml of Milli-Q-purified water (18 MΩ·cm resistivity) was dropwise added to the polymer solution at a rate of 0.05 ml/min using a syringe pump, and the mixture was kept under vigorous stirring for 24 hours. To remove the acetone, the solution was transferred to a dialysis bag (Spectra/Por 7, 50 kDa molecular weight cutoff), and dialyzed for 3 hours against 1 L Milli-Q-purified water. The reservoir was replaced with fresh Milli-Q water every hour.

Polymer Micelle Characterizations

The hydrodynamic diameters of the block copolymer micelles were measured at 25° C. by Dynamic Light Scattering (DLS) using a Brookhaven ZetaPALS instrument. The scattering intensities were measured using a 659 nm laser at a scattering angle of 90°. The hydrodynamic diameters were calculated from the measured diffusion coefficients using the Stokes-Einstein equation. For DLS measurements, the samples were diluted to guarantee single scattering, and were filtered with 0.2-μm syringe filters to remove contaminants.

Transmission Electron Microscopy (TEM) was used to image the polymer micelles. TEM specimens were prepared by placing 20 μl of a 0.01-0.05 mg/ml polymer micelle solution on a carbon-coated copper TEM grid (hydrophobically treated using a $O_2$ plasma cleaner). 10 μl of a 2% uranyl acetate solution was added to the sample solution already placed on the TEM grid, and the mixture was blotted using filter paper and dried. The samples thus prepared were imaged using a 200 kV FEI Tecnai 20 TEM instrument. The TEM images were analyzed using the Gatan Digital Micrograph software.

NMR Spin Relaxation Measurements

NMR spin relaxation measurements were performed using a Bruker Avance-III-800 Spectrometer equipped with a sample temperature control unit. PLGA-PEG and PS-PEG micelle samples were prepared using the solvent exchange procedure (described above) using $D_2O$ (instead of $H_2O$) as the final solvent. The PEG homopolymer sample was prepared by directly dissolving PEG in $D_2O$. In all samples, the polymer concentration was 0.5 wt. %. The inversion recovery sequence was used for $T_1$ relaxation measurements, and the Carr-Purcell-Meiboom-Gill (CPMG) pulse sequence was used for $T_2$ relaxation measurements. Data were fit to single or biexponential decay functions using the nonlinear least squares regression technique.

Evaluation of the Tolerability of Intratracheally Injected Polymer LSs in Adult Mice In this study, C57/BL6 mice (8-12 weeks old, female) were used. Prior to intratracheal instillation of polymer LSs, mice were anesthetized using isoflurane. Mice were then placed on a custom-designed angled platform with its incisors hung on a wire. The tongue was pulled out of the mouse using forceps, and 4 ml of polymer LS solutions per kg body weight containing different concentrations of polymers were directly dropped into the opening of the trachea using a micropipette. Mice were left to naturally recover from anesthesia.

For the MTD evaluation, mice were intratracheally instilled with three different doses of PS(4418)-PEG(5000) micelles (2.4, 24 and 240 mg/kg), and examined for 2 weeks for symptoms of toxicity (weight loss, activity level, etc.). After day 14, mice were humanely sacrificed.

For bronchoalveolar lavage (BAL) fluid/histology analysis, mice were sacrificed at day 7 following intratracheal instillation of 240 mg PS(4418)-PEG(5000) micelles per kg body weight. BAL fluids were collected by injecting and recovering two 0.6 ml aliquots of ice-chilled phosphate-buffered saline. Two aliquots were combined and centrifuged at 150×g and 4° C. for 10 minutes to remove cells and particles. Levels of albumin and four immune makers (IFN-γ, TNF-α, MCP-5 and IL-6 cytokines) in the BAL fluid samples were analyzed using the method described in Reference.

Closed Chest Pressure-Volume (PV) Analysis of Acid-Injured Mouse Lungs After Treatment with Polymer LSs C57/BL6 mice (8-12 weeks old, female) were used in this study. Acute lung injury was produced by intratracheal installation of 30 μl of 0.25 N HCl using the procedure described above. At 5 hours post acid aspiration, mice were intratracheally instilled with 3 ml/kg of Infasurf (35 mg/ml), 4 ml/kg of PS(4418)-PEG(5000) micelles (0.6, 6 or 60 mg/ml), or 4 ml/kg of 0.9% saline. At 10 minutes following LS treatment, mice were sacrificed using excess ketamine. Immediately after sacrifice, the mice trachea was cut open by surgical incision, and connected to a Flexivent® SCIREQ ventilator through an 18-gauge blunt-end needle (inserted into the trachea). A prescribed ventilation sequence was executed to obtain closed chest pressure-volume curves. Details of the ventilation setup and parameters used can be found in Reference.

Preliminary Evaluation of the Tolerability of Intratracheally Injected Polymer Lung Surfactants in Adult Mice In this study, 7-weeks old female BALB/C mice (purchased from Jackson Laboratory) were used. Prior to injection of polymer lung surfactants, mice were analgetized by injecting 80 μl of 0.75 mg/ml Prevail (VetOne) to the back of the mouse neck. Mice were then anesthetized using isoflurane at 2 l/min flow rate. Once mice were completely sedated, tracheotomy was performed to inject the polymer lung surfactant solution. Three different doses were tested: 0.64, 6.5 and 64 mg polymer per kg mouse body weight. The liquid injection volume was kept at 20 μl, which corresponded to 1.07 ml liquid per kg body weight. After polymer injection, mice were sutured, and GLUture (Abbott Laboratories) was applied to the surgery area. Mice were monitored by experienced animal technicians for indications of toxicity (weight loss and behavioral symptoms).

After day 14, mice were sacrificed, and major organs were collected, perfused with PBS, and fixed with 10% formalin. For the preparation of lung tissue an additional step was applied: inflation of the excised lung with 10% formalin prior to fixation. The collected organ tissues were sliced and stained with H&E for microscopy examination.

Pressure-Volume (PV) Mechanics of Rabbit Fetus Lungs Following Administration of Polymer Lung Surfactants P-V mechanics of 27-day gestation New Zealand White Rabbit fetus lungs were tested ex vivo following administration of polymer lung surfactants. Fetuses were obtained by Cesarean section. Polymer lung surfactants (or Newfacten) were injected into the rabbit fetus lung by single intratracheal instillation of 1.5 ml liquid per kg body weight. Polymer lung surfactant doses tested were 6, 60 and 96 mg polymer per kg body weight, and the Newfacten dose was 60 mg/kg. After lung surfactant instillation, 10 minutes were waited before PV analysis.

Based on the above description, we can now disclose a method of treating pulmonary disorders, including infant, acute or adult respiratory distress syndromes, caused by deficiency and/or deactivation of functional lung surfactant in mammals, including humans. The method includes administering to an animal or human subject a therapeutically effective amount of polymer lung surfactant composition. The polymer lung surfactant composition comprises an effective amount of a synthetic biocompatible or biodegradable amphiphilic homopolymer or copolymer whose monomers are selected from the group consisting of: ethylene glycol (EG), ethylene oxide (EO), vinyl alcohol (VA), alkyl oxazoline (AO), D,L-lactic acid or D,L-lactide (LA), glycolic acid or glycolide (GA), ε-caprolactone (CL), styrene (PS), alkyl methacrylate (AMA), alkyl acrylate (AA), butadiene (BD), and isoprene (IP).

Another method of treating pulmonary disorders, including infant, acute or adult respiratory distress syndromes, caused by deficiency and/or deactivation of functional lung surfactant in mammals, including humans, wherein the method includes administering to an animal or human subject a synthetic block copolymer as a single therapeutic agent or in combination with other therapeutics.

Yet another method of treating pulmonary disorders, including infant, acute or adult respiratory distress syndromes, caused by deficiency and/or deactivation of functional lung surfactant in mammals, including humans, includes administering to an animal or human subject a synthetic random copolymer to the subject as a single therapeutic agent or in combination with other therapeutics.

Another method of treating pulmonary disorders, including infant, acute or adult respiratory distress syndromes, caused by deficiency and/or deactivation of functional lung surfactant in mammals, including humans, wherein the method includes administering to an animal or human subject a synthetic homopolymer to the subject as a single therapeutic agent or in combination with other therapeutics.

Yet another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(styrene-block-ethylene glycol) (PS-PEG) block copolymer.

Another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(tert-butyl methacrylate-block-ethylene glycol) (PtBMA-PEG) block copolymer.

Another method of treating pulmonary disorders, including infant, acute or adult respiratory distress syndromes, caused by deficiency and/or deactivation of functional lung surfactant in mammals, including humans, wherein the method includes administering to an animal or human subject a polymer lung surfactant composition comprising a poly(D,L-lactic acid-block-ethylene glycol) (PLA-PEG) block copolymer.

A method of treating pulmonary disorders, including infant, acute or adult respiratory distress syndromes, caused by deficiency and/or deactivation of functional lung surfactant in mammals, including humans, wherein the method includes administering to an animal or human subject, a polymer lung surfactant composition to the lungs of the animal or human subject in the form of an aqueous solution via endotracheal instillation.

A method of treating pulmonary disorders, including infant, acute or adult respiratory distress syndromes, caused by deficiency and/or deactivation of functional lung surfactant in mammals, including humans, wherein the method includes including administering to an animal or human subject a polymer lung surfactant composition to the patient's lungs in the form of liquid drop or lyophilized powder-type aerosols through application of continuous positive airway pressure.

Exemplary polymer lung surfactant composition used in above method of treatment have a formulation comprising, at the time of administration to a patient, about 0.02-40 wt. % amphiphilic block copolymers dispersed in micelle form in aqueous saline solution, wherein the amphiphilic block copolymer compound comprises a hydrophilic block (e.g., PEG) having an average molecular weight in the range between about 50 Da and about 1000 kDa and a hydrophobic block (e.g., PS) having an average molecular weight in the range between about 50 Da and about 1000 kDa.

It should be note that all the above described methods can be used in treating infant, acute or adult respiratory distress syndromes. Further, these methods can also be used in treating bronchopulmonary dysplasia.

Those skilled in the art will recognize that numerous modifications can be made to the specific implementations described above. The implementations should not be limited to the particular limitations described. Other implementations may be possible. In addition, several publications relevant to the disclosure are listed below and are cited herein. The contents of these references are hereby incorporated by reference in their entirety into this disclosure.

The invention claimed is:

1. A method of treating a pulmonary disorder of a mammal caused by deficiency and/or deactivation of functional lung surfactant in said mammal, the method comprising:

administering to said mammal a therapeutically effective amount of a polymer lung surfactant composition, wherein the polymer lung surfactant composition comprises a synthetic biocompatible amphiphilic block copolymer, wherein the hydrophilic (water soluble) block comprises a monomer selected from the group consisting of ethylene glycol (EG), ethylene oxide (EC), vinyl alcohol (VA), and oxazoline (OZ), wherein the hydrophobic (water-insoluble) block copolymer comprises a monomer selected from the group consisting of lactic acid or lactide (LA), glycolic acid or glycolide (GA), caprolactone (CL), styrene (S), methacrylate (MA), acrylate (Ac), butadiene (BD), and isoprene (IP), and wherein said polymer lung surfactant composition forms stable micelles in aqueous solution, wherein the micelles are used in uncomplexed form not loaded with any other therapeutic agents.

2. The method of claim 1, wherein said pulmonary disorder is a neonatal respiratory distress syndrome (NRDS) or acute respiratory distress syndrome (ARDS) caused by deficiency and/or deactivation of functional lung surfactant.

3. The method of claim 1, wherein the block copolymer lung surfactant composition comprises at least one polymerized hydrophobic block comprising methacrylate and at least one polymerized hydrophilic block comprising ethylene glycol.

4. The method of claim 1, wherein the block copolymer lung surfactant composition comprises at least one polymerized hydrophobic block comprising lactic acid or lactide and at least one polymerized hydrophilic block comprising ethylene glycol.

5. The method of claim 1, wherein the block copolymer lung surfactant composition comprises at least one polymerized hydrophobic block comprising butadiene and at least one polymerized hydrophilic block comprising ethylene glycol.

6. The method of claim 1, wherein the therapeutically effective amount of the polymer lung surfactant composition is administered to the lungs of said mammal in the form of an aqueous solution via endotracheal instillation.

7. The method of claim 1, wherein the therapeutically effective amount of the polymer lung surfactant composition is administered to the lungs of said mammal in the form of liquid drop or lyophilized powder-type aerosols through application of continuous positive airway pressure or mechanical ventilation.

8. The method of claim 7, wherein the therapeutically effective amount of the polymer lung surfactant composition is administered to the lung in combination with other therapeutics, wherein said other therapeutics are not loaded within or do not form complexes with micelles formed by said polymer lung surfactant.

* * * * *